US011547719B2

(12) United States Patent
Park et al.

(10) Patent No.: US 11,547,719 B2
(45) Date of Patent: Jan. 10, 2023

(54) ACETYLATION OF ALOE POLYSACCHARIDES

(71) Applicant: HERBALIFE INTERNATIONAL OF AMERICA, INC., Los Angeles, CA (US)

(72) Inventors: Joosang Park, Los Angeles, CA (US); Zhichao Bao, Los Angeles, CA (US); Qunyi Zheng, Los Angeles, CA (US); Kan He, Los Angeles, CA (US); Troy Smillie, Los Angeles, CA (US); Zhaoyang Xie, Los Angeles, CA (US)

(73) Assignee: Herbalife International of America, Inc., Los Angeles, CA (US)

( * ) Notice: Subject to any disclaimer, the term of this patent is extended or adjusted under 35 U.S.C. 154(b) by 0 days.

(21) Appl. No.: 17/034,672

(22) Filed: Sep. 28, 2020

(65) Prior Publication Data

US 2021/0008098 A1   Jan. 14, 2021

Related U.S. Application Data

(63) Continuation of application No. PCT/US2019/024104, filed on Mar. 26, 2019.

(60) Provisional application No. 62/649,344, filed on Mar. 28, 2018.

(51) Int. Cl.
*A61K 31/736* (2006.01)
*C08B 37/00* (2006.01)
*A61P 37/02* (2006.01)

(52) U.S. Cl.
CPC ............ *A61K 31/736* (2013.01); *A61P 37/02* (2018.01); *C08B 37/0087* (2013.01)

(58) Field of Classification Search
CPC .... C08B 37/0087; A61K 31/736; A61P 37/02
See application file for complete search history.

(56) References Cited

U.S. PATENT DOCUMENTS

| 5,106,616 | A | 4/1992 | McAnalley et al. |
|---|---|---|---|
| 5,441,943 | A | 8/1995 | McAnalley et al. |
| 5,445,829 | A | 8/1995 | Paradissis et al. |
| 5,576,012 | A | 11/1996 | Bauer et al. |
| 5,601,845 | A | 2/1997 | Buxton et al. |
| 5,641,515 | A | 6/1997 | Ramtoola |
| 5,653,987 | A | 8/1997 | Modi et al. |
| 5,654,286 | A | 8/1997 | Hostetler |
| 5,667,809 | A | 9/1997 | Trevino et al. |
| 5,683,676 | A | 11/1997 | Akehurst et al. |
| 5,688,529 | A | 11/1997 | Lidgate et al. |
| 5,703,060 | A | 12/1997 | McAnalley et al. |
| 5,707,615 | A | 1/1998 | Cardin et al. |
| 5,707,641 | A | 1/1998 | Gertner et al. |
| 5,726,181 | A | 3/1998 | Hausheer et al. |
| 5,733,888 | A | 3/1998 | Carver et al. |
| 5,780,453 | A | 7/1998 | McAnalley et al. |
| 5,824,659 | A | 10/1998 | Strickland et al. |
| 6,133,440 | A | 10/2000 | Qiu et al. |
| 6,251,878 | B1 | 6/2001 | Strickland et al. |
| 7,196,072 | B2 | 3/2007 | Pasco et al. |
| 2009/0197789 | A1 | 8/2009 | Brooker et al. |
| 2012/0022018 | A1 | 1/2012 | Danhof |
| 2017/0159036 | A1 | 6/2017 | Adams |

FOREIGN PATENT DOCUMENTS

| CA | 2122604 | 5/1993 |
|---|---|---|
| CA | 1339113 | 7/1997 |
| CN | 1169838 | 10/2004 |
| CN | 101948550 | 5/2012 |
| CN | 103734854 | 4/2014 |
| CN | 103766915 | 5/2014 |
| CN | 103767032 | 5/2014 |
| CN | 104693314 | 6/2015 |
| CN | 104693315 | 6/2015 |
| DE | 691 31 628 | 11/1991 |
| KR | 10-1183732 | 9/2012 |
| WO | WO 92/019753 | 11/1992 |
| WO | WO 93/08810 | 5/1993 |
| WO | WO 15/070060 | 5/2015 |

OTHER PUBLICATIONS

Koroskenyi et al., Biomacromolecules, 2001, 2, p. 824-826. (Year: 2001).*
Yao-ling et al., Journal of Single Molecule Research, 2013, 1(1), p. 7-14. (Year: 2013).*
Tatirat et al., LWT—Food Science and Technology, 2011, 44, p. 2059-2063. (Year: 2011).*
Xu et al., Carbohydrate Research, 2010, 345, p. 810-816. (Year: 2010).*
Extended European Search Report dated Dec. 9, 2021 in patent application No. 19776799.9.
Alm et al., 1989, Effects of topically applied $PCG_{2\alpha}$ and its isopropylester on normal and glaucomatous human eyes, Prog. Clin. Biol. Res., 312:447-458.
Joshi, 1994, Microparticulates for ophthalmic drug delivery, J. Ocul. Pharmacol., 10(1):29-45.
Koschella et. al., 2012, Synthesis and characterization of branched polysaccharides by reaction of cellulose with 2,3,4,6-tetraacetyl-1-bromo-α-D-glucopyranoside, ARKIVOC 2012 (iii) 76-89.
Mayer et al., 1996, Efficacy of a novel hydrogel formulation in human volunteers, Ophthalmologica, 210(2):101-103.

(Continued)

*Primary Examiner* — Jonathan S Lau
(74) *Attorney, Agent, or Firm* — Knobbe, Martens, Olson & Bear, LLP

(57) ABSTRACT

Acetylated polysaccharides and methods of making and using them are provided. One method of making acetylated polysaccharides includes providing polysaccharides, purifying the polysaccharides to 1-90% purity by weight, providing an acetylation agent, providing a catalyst, mixing the acetylation agent and catalyst with the polysaccharides, thereby manufacturing acetylated polysaccharides, and purifying the acetylated polysaccharides.

10 Claims, 11 Drawing Sheets

(56) References Cited

OTHER PUBLICATIONS

Mordenti et al., 1999, Intraocular pharmacokinetics and safety of a humanized monoclonal antibody in rabbits after intravitreal administation of a solution or a PLGA microsphere formulation, Toxicol. Sci., 52(1):101-106.

Qi et al.,Dec. 4, 2010, In vitro antioxidant activity of acetylated derivatives of polysaccharide extracted from Ulva pertusa (Cholorophta), Journal of Medicinal Plants Research, 4(23):2445-2451.

Shedden et al., 2001, Efficacy and toleraabilty of timolol maleate ophthalmic gel-forming solution versus timolo ophthalmic solution in adults with open-angle glaucoma or ocular hypertension: a six-month, double-masked, multicenter study, Clin. Ther., 23(3):440-450.

Yuan et al., 2005, Preparation and in vitro antioxidant activity of κ-carrageenan oligosaccharides and their oversulfated, acetylated and phosphorylated derivatives. Carbohydr. Res., 340: 685-692.

International Search Report and Written Opinion dated Jun. 3, 2019 in application No. PCT/US2019/024104.

Chokboribal et al., 2015, Deacetylation affects the physical properties and bioactivity of acemannan, an extracted polysaccharide from Aloe vera, Carbohydrate Polymers, 133:566-566.

Dominguez-Fernandez et al., 2012, Aloe vera gel: structure, chemical composition, processing, biological activity and importance in pharmaceutical and food industry. Rev. Mex. Ing. Quím [online]. 11(1):23-43 (abstract).

* cited by examiner

ACETYLATION OF ALOE POLYSACCHARIDES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The embodiments as described herein, relate to methods of increasing the amount of acetylation in polysaccharides, acetylated polysaccharides and methods of treatment. Particularly, the polysaccharides are derived from plants or plant parts thereof. When plant parts are subjected to the manufacturing processes to extract their polysaccharides, such purification processes lead to the deacetylation of the natural plant polysaccharides. As described herein, are methods that increase the amount of acetylation in plant polysaccharides after process manufacturing methods, such that the levels of acetylation exceed the acetylation amount in polysaccharides that was originally found in the natural plant polysaccharide.

DESCRIPTION OF THE RELATED ART

Polysaccharides are natural resources for supplements and pharmaceuticals that have received more and more attention over the years. Natural polysaccharides have been shown to have fewer side effects, but because of their inherently physicochemical properties, their bioactivities were difficult to compare with those of synthetic drugs. Thus, researchers have modified the structures and properties of natural polysaccharides based on structure-activity relationships and have obtained better functionally improved polysaccharides. However, major modification methods of polysaccharides can be necessary as they can affect their physicochemical properties and bioactivities. Molecular modification methods mainly include chemical, physical, and biological changes. Chemical modification is the most widely used method; it can significantly increase the water solubility and bioactivities of polysaccharides by grafting onto other groups. Physical and biological modifications only change the molecular weight of a polysaccharide, and thereby change its physicochemical properties and bioactivities. Most of the molecular modifications bring about an increase in the antioxidant activity of polysaccharides, and among these, sulfated and acetylated modifications are very common. Furthermore, modification is the most common application to increase anti-inflammatory activities as discussed herein.

BACKGROUND

This field is related to the processing of plants and plant parts for the development of acetylated sugars or carbohydrates for therapeutic use. Also described herein are efficient methods of obtaining highly acetylated sugars or carbohydrates that have been extracted from plants and/or plant parts.

*Aloe vera* is a succulent plant species of the genus *Aloe*. It grows wild in tropical climates around the world and is cultivated for agricultural and medicinal uses. *Aloe vera* has been widely recognized in the cosmetic and alternative medicine industries for its moisturizing and healing properties.

*Aloe vera* has been used for decades to soothe irritation such as dry skin, or pain from a sunburn. Extraction and characterization of the *aloe vera* gel has revealed that the gel comprises many types of mucopolysaccharides.

In medical practices, polysaccharides have been known as signaling molecules that may account for their therapeutic properties. Gel forming complex carbohydrates have been known to act as a demulcent or emollient. In some instances, several types have been recognized as being anti-inflammatory and immune modulators.

The polysaccharide, acemannan, is a polysaccharide composed by a mainly backbone of $\beta$-(1→4)-linked D-mannose residues interspersed by few glucose residues, acetylated in O-2, O-3, O-2/O-3, or O-6 containing side chains constituted by O-6-linked single $\alpha$-D-galactose and $\alpha$-L-arabinose residues. *Aloe vera* acemannan may present immunostimulatory activity. A study of the structural details of the polysaccharide has shown that acemannan presents a complex acetylation pattern. However, during extraction and processing of the polysaccharide, the polysaccharide can become deacetylated. Acetylated polysaccharides have been attributed to the promotion of the immunomodulatory activity. As such, methods are needed to efficiently acetylate the hydroxyl groups of this polysaccharide at a high content in order to preserve its immunomodulatory activity.

SUMMARY

In a first aspect, a method of making acetylated polysaccharides is provided. The method comprises a) providing polysaccharides; b) purifying the polysaccharides to 90% purity by weight; c) providing an acetylation agent; d) providing a catalyst; e) mixing the acetylation agent and catalyst with the polysaccharides, thereby manufacturing acetylated polysaccharides, wherein the acetylation exceeds that of the polysaccharides in step a); and f) purifying the acetylated polysaccharides. In some embodiments, the resulting polysaccharides feature acetylation exceeding that of naturally occurring polysaccharides. In some embodiments, the polysaccharides are from plants or plant parts thereof. In some embodiments, the polysaccharides are in a powder formulation. In some embodiments, the polysaccharides are from an extraction process from the plants or plant parts thereof, In some embodiments, the plants or parts thereof comprises a whole leaf powdered extract or a plant inner clear gel powdered extract. In some embodiments, the plant is a succulent plant of the genus *Aloe*. In some embodiments, the plant parts thereof comprise outer green rind and/or plant inner clear gel. In some embodiments, the polysaccharides comprises glucomannan, glucogalactomannan, galactomannan, mannan and their acetylating forms. In some embodiments, the polysaccharides comprise hydroxyl groups, wherein the hydroxyl groups are capable of being substituted with acetyl groups. In some embodiments, the polysaccharides comprise mannose moieties. In some embodiments, the mannose moieties comprise hydroxyl groups, wherein the hydroxyl groups are capable of being acetylated. In some embodiments, the actylated polysaccharide comprises acetyl groups on the mannose moieties at mannose sites 2, 3 and/or 6. In some embodiments, the polysaccharides are purified to 1-90% purity by weight. In some embodiments, the polysaccharides are purified to 90% purity by weight. In some embodiments, the acetylated polysaccharides are purified to 90% purity by weight. In some embodiments, the method further comprises determining contents of the acetylated polysaccharides and positions of acetyl groups on the acetylated polysaccharides. In some embodiments, the determining is performed by Infrared spectroscopic (IR) and/or nuclear magnetic resonance (NMR) spectroscopic methods. In some embodiments, the acetylation agent is acetic anhydride $(CH_3CO)_2O$, acetyl chloride or acetic acid. In some embodiments, the catalyst is pyridine, sodium hydroxide, potassium hydroxide, sodium carbonate, or potassium carbonate and/or solvent. In some embodiments, the purifying step of step b) is performed by ethanol precipitation. In some embodiments, the purifying step of step d) is performed by dialysis.

In a second aspect, an acetylated polysaccharide manufactured from the methods of any one of the embodiments herein is provided. In some embodiments, the method comprises a) providing polysaccharides; b) purifying the polysaccharides to 90% purity by weight; c) providing an acetylation agent; d) providing a catalyst; e) mixing the acetylation agent and catalyst with the polysaccharides, thereby manufacturing acetylated polysaccharides, wherein the acetylation exceeds that of the polysaccharides in step a); and f) purifying the acetylated polysaccharides. In some embodiments, the resulting polysaccharides feature acetylation exceeding that of naturally occurring polysaccharides. In some embodiments, the polysaccharides are from plants or plant parts thereof. In some embodiments, the polysaccharides are in a powder formulation. In some embodiments, the polysaccharides are from an extraction process from the plants or plant parts thereof, In some embodiments, the plants or parts thereof comprise a whole leaf powdered extract or a plant inner clear gel powdered extract. In some embodiments, the plant is a succulent plant of the genus *Aloe*. In some embodiments, the plant parts thereof comprise outer green rind and/or plant inner clear gel. In some embodiments, the polysaccharides comprises glucomannan, glucogalactomannan, galactomannan, mannan and/or their acetylating forms. In some embodiments, the polysaccharides comprise hydroxyl groups, wherein the hydroxyl groups are capable of being substituted with acetyl groups. In some embodiments, the polysaccharides comprise mannose moieties. In some embodiments, the mannose moieties comprise hydroxyl groups, wherein the hydroxyl groups are capable of being acetylated. In some embodiments, the actylated polysaccharide comprises acetyl groups on the mannose moieties at mannose sites 2, 3 and/or 6. In some embodiments, the polysaccharides are purified to 1-90% purity by weight. In some embodiments, the polysaccharides are purified to 90% purity by weight. In some embodiments, the acetylated polysaccharides are purified to 90% purity by weight. In some embodiments, the method further comprises determining contents of the acetylated polysaccharides and positions of acetyl groups on the acetylated polysaccharides. In some embodiments, the determining is performed by Infrared spectroscopic (IR) and/or nuclear magnetic resonance (NMR) spectroscopic methods. In some embodiments, the acetylation agent is acetic anhydride $(CH_3CO)_2O$, acetyl chloride or acetic acid. In some embodiments, the catalyst is pyridine, sodium hydroxide, potassium hydroxide, sodium carbonate, or potassium carbonate and solvent. In some embodiments, the purifying step of step b) is performed by ethanol precipitation. In some embodiments, the purifying step of step d) is performed by dialysis. In some embodiments, the acetylated polysaccharide comprises at least one, two, or three acetyl groups. In some embodiments, the acetylated polysaccharide comprises mannose groups. In some embodiments, the polysaccharide comprises glucomannan, glucogalactomannan, galactomannan, mannan and/or their acetylating forms.

In a third aspect, a pharmaceutical formulation comprising an acetylated polysaccharide of any one of the embodiments provided herein or an acetylated polysaccharide manufactured by the method of any one of the embodiments provided herein and a pharmaceutically acceptable excipient is provided. In some embodiments, the formulation is a pill. In some embodiments, the formulation is a liquid. In some embodiments, the formulation is a tablet, gummy, capsule, or lozenge. In some embodiments, the formulation further comprises nontoxic auxiliary substances, such as wetting agents, pH buffering agents, and absorption enhancing preparations.

In a fourth aspect, a method of treating, ameliorating or preventing an inflammatory response in a subject in need thereof is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the acetylated polysaccharide is administered at least three times a day, twice a day, once a day, once a week or once a month. In some embodiments, the patient is suffering from an immune disorder. In some embodiments, the immune disorder is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease or Ataxia-telangiectasia. In some embodiments, the patient is identified to receive a therapeutic for inflammation. In some embodiments, the patient is identified to receive a therapeutic for an immune disorder. In some embodiments, the method further comprises measuring or evaluating an inhibition of the inflammatory response. In some embodiments, the method further comprising providing said subject an additional therapeutic before, during, or after administration of the acetylated polysaccharide of any one of the embodiments herein or the acetylated polysaccharide manufactured by the method of the embodiments herein or the pharmaceutical formulation of the embodiments herein. In some embodiments, the subject is a patient. In some embodiments, the patient is a subject. In some embodiments, the subject is a mammal. In some embodiments, the subject is a human, horse, dog, cat.

In a fifth aspect a method of treating an immune disorder in a subject in need thereof is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the acetylated polysaccharide is administered at least three times a day, twice a day, once a day, once a week or once a month. In some embodiments, the immune disorder is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease or Ataxia-telangiectasia.

In a sixth aspect, a method of increasing the expression of anti-inflammatory IL-10 (interleukin 10) in a subject in need is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the acetylated polysaccharide is administered at least three times a day, twice a day, once a day, once a week or once a month. In some embodiments, the patient is suffering from an immune disorder. In some embodiments, the method further comprises monitoring the expression of anti-inflammatory IL-10 (interleukin 10). In some embodiments, the subject in need is a mammal. In some embodiments, the subject is a human, horse, dog, cat.

In a seventh aspect, a method of elevating the expression of an anti-inflammatory cytokine in a subject in need is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the acetylated polysaccharide is administered at least three times a day, twice a day, once a day, once a week or once a month. In some embodiments, the patient is suffering from an immune disorder. In some embodiments, the method further comprises monitoring the expression of anti-inflammatory. In some embodiments, the subject in need is a mammal. In some embodiments, the subject is a human, horse, dog, cat. In some embodiments, the anti-inflammatory cytokine is selected from a group consisting of interleukin (IL)-1 receptor antagonist, IL-4, IL-6, IL-10, IL-11, and IL-13.

In an eighth aspect, a method of treating tumor in a subject in need thereof is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the acetylated polysaccharide is administered at least three times a day, twice a day, once a day, once a week or once a month. In some embodiments, the patient is suffering from cancer. In some embodiments, the tumor is from lung cancer, skin cancer, liver cancer, brain cancer, kidney cancer, uterine cancer. In some embodiments, the patient is identified to receive a therapeutic for cancer. In some embodiments, the method further comprises measuring or evaluating tumor growth. In some embodiments, the method further comprises providing said subject an additional therapeutic before, during, or after administration of the acetylated polysaccharide of any one of the embodiments herein or the acetylated polysaccharide manufactured by the method of any one of the embodiments herein or the pharmaceutical formulation of any one of any one of the embodiments herein. In some embodiments, the subject is a mammal. In some embodiments, the subject is a human, horse, dog, cat.

In a ninth aspect, a method of treating a viral or bacterial infection in a subject in need is provided. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the method further comprises monitoring levels of cytokines released during the viral or bacterial infection. The method comprises administering to the patient in need thereof, an acetylated polysaccharide of any one of the embodiments provided herein or an acetylated polysaccharide manufactured by the method of any one of the embodiments provided herein or the pharmaceutical formulation of any one of the embodiments provided herein. In some embodiments, the cytokines are selected from a group consisting of IL-1beta, IL-6, IL-7, IL-8, IL-10, tumor necrosis factor (TNF)-alpha, interferon (IFN)-gamma and IFN-alpha/beta.

In some embodiments, the acetylated polysaccharide has a molecular weight in the range of about 1 to about 70 kilodaltons. In some embodiments, the acetylated polysaccharide has a molecular weight in the range of about 5 to about 50 kilodaltons. In some embodiments, the acetylated polysaccharide has a molecular weight in the range of about 10 to about 40 kilodaltons. In some embodiments, the acetylated polysaccharide has a molecular weight in the range of about 15 to about 30 kilodaltons. In some embodiments, the acetylated polysaccharide has a molecular weight of about 18 kilodaltons. In some embodiments, the acetylated polysaccharide has a molecular weight of about 29 kilodaltons. In some embodiments, the acetylated polysaccharide has a molecular weight of less than, greater than, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 kilodaltons or any number or range therebetween.

BRIEF DESCRIPTION OF THE DRAWINGS

The features and advantages of the compositions, systems, devices, and methods described herein will become apparent from the following description, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

FIG. 1A) General structure of native *aloe* glucomannan inserted with glucosyl with 1, 4-β-linked backbone and acetylated at positions of 2, 3, or 6; FIG. 1B) polysaccharides with fewer acetyl groups after processing; FIG. 1C) highly acetylated polysaccharides after acetylation. Manp: mannopyranosyl; Glcp: glucopyranosyl.

DEFINITIONS

Figure 1A:
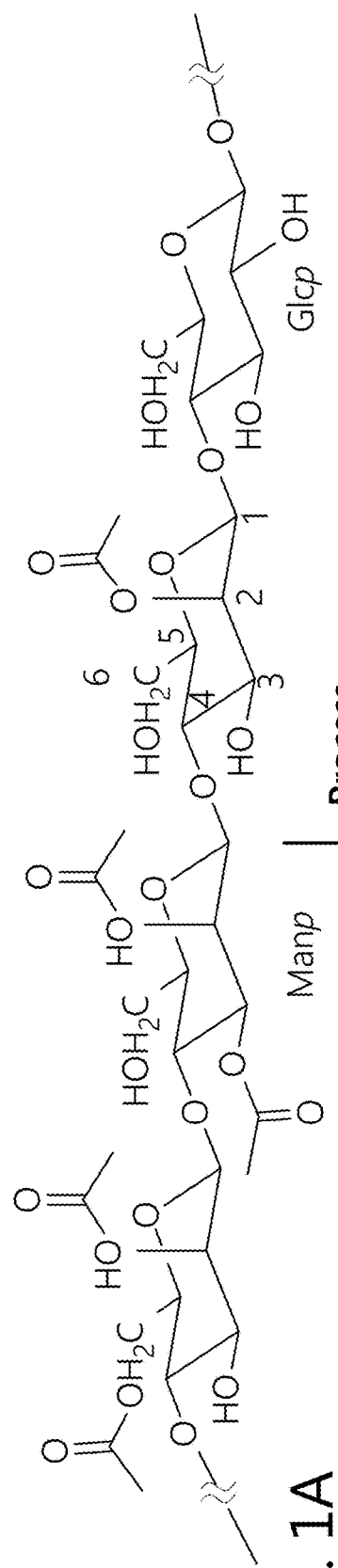
FIGS. 1A-1C show the process of acetylating native *aloe* glucomannan.
Figure 1B:
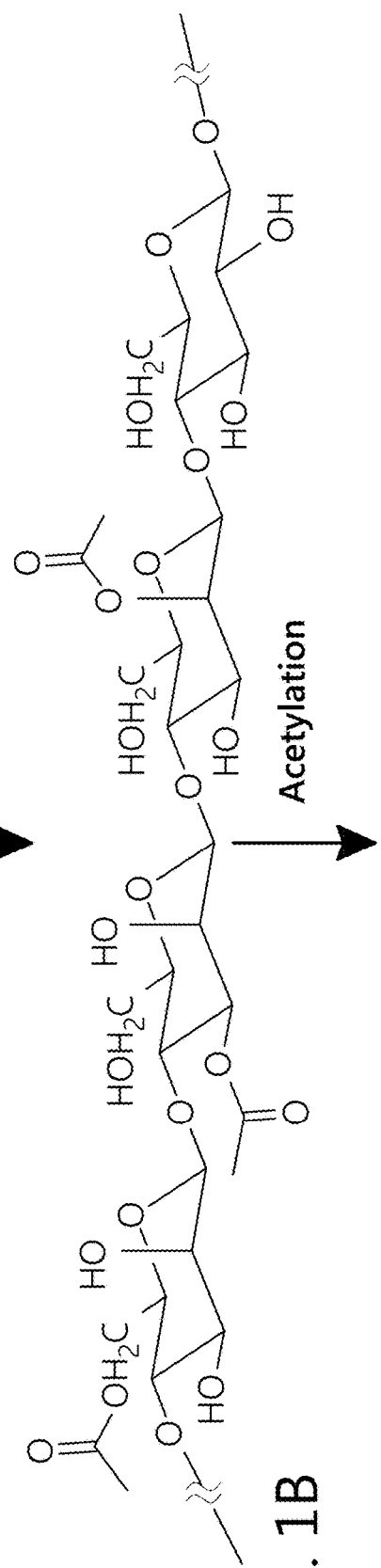
Figure 1C:
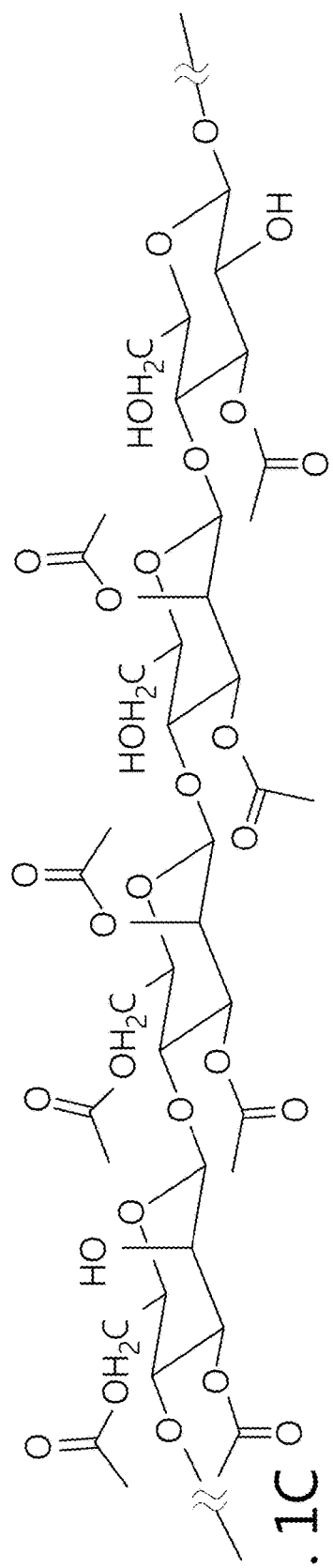

"Polysaccharides," as described herein, are polymeric carbohydrate molecules composed of long chains of monosaccharide units bound together by glycosidic linkages. During hydrolysis these polysaccharides breach into constituent monosaccharides or oligosaccharides. Polysaccharides can range in structure from linear to highly branched polysaccharides. There are several types of polysaccharides. Without being limiting, polysaccharides can include structural polysaccharides, neutral polysaccharides, acidic polysaccharides, bacterial capsular polysaccharides, and storage polysaccharides. The function of polysaccharides in living organisms such as plants can be for either structure-or storage-related. Starch (a polymer of glucose) is used as a storage polysaccharide in plants, being found in the form of both amylose and the branched amylopectin.

"Purification" is a technique known to those skilled in the art in which a compound, chemical, protein or DNA, as a substance from foreign or contaminating substances. Without being limiting purification can be performed by affinity purification, filtration, evaporation, liquid-liquid extraction, crystallization, recrystallization and fractionation. In some embodiments, the crude polysaccharides are purified to 1-90% purity by weight. In some embodiments herein, crude polysaccharides are purified to a 90% purity by weight. In some embodiments herein, the acetylated product is purified to a 90% purity by weight. In some embodiments a product produced by the described methods herein, is purified by ethanol precipitation. In some embodiments the purification is performed by dialysis.

"Glucomannan," as described herein is a major polysaccharide in aloe, consisting of mannose and glucose with 1, 4-β-linked backbone, where the mannose is predominant.

"Acetylation" as described herein, refers to a reaction that introduces an acetyl functional group into a chemical compound. Acetylation refers to the process of introducing an acetyl group (resulting in an acetoxy group) into a compound, namely the substitution of an acetyl group for an active hydrogen atom. In some embodiments herein, a polysaccharide is acetylated at a hydroxyl group. The term "acetyl" refers to a "—C(=O)CH$_3$" group.

"Acetylation agent" as described herein, is a chemical used in the acetylation of a chemical compound. Without being limiting, acetylation can occur with acid anhydride in the presence of acid or base catalysts. Various metal salts such as $CoCl_2$, $TiCl_4$—$AgClO_4$, TaCl and $TaCl_5$—$SiO_2$, Ce(III) triflate, Sn(IV) porphyrine and some metal triflates such as $Sc(OTf)_3$, MeSiOTf, $In(OTf)_3$, $Cu(OTf)_2$ and $Bi(OTf)_3$, bis(cyclopentadienyl) zirconium dichloride, $I_2$, 1,3-dibromo-5,5-dimethylhydentoin or trichloroisocyanuric acid can also be used in a reaction for efficiency.

"Catalysis" as described herein is the increase in the rate of a chemical reaction in the presence of an additional substance called a "cataylst." As described herein, methods used for acetylation can also be provided with a catalyst. In some embodiments herein, the catalyst is pyridine, sodium hydroxide, potassium hydroxide, sodium carbonate, or potassium carbonate and solvent.

"Infrared spectroscopy" (IR spectroscopy or Vibrational Spectroscopy), as described herein, is the spectroscopy that deals with the infrared region of the electromagnetic spectrum, that is light with a longer wavelength and lower frequency than visible light. It covers a range of techniques, mostly based on absorption spectroscopy. IR spectroscopy is known to those skilled in the art and can be used in the identification and characterization of chemical compounds and chemicals. In some embodiments herein, IR spectroscopy is used to determine the contents of a polysaccharide or to characterize a polysaccharide.

"Nuclear magnetic resonance spectroscopy" or "NMR spectroscopy," as described herein, is a research technique that exploits the magnetic properties of certain atomic nuclei. It can be used determine the physical and chemical properties of atoms or the molecules in which they are contained. An analysis of 1D, 2D or 3D NMR spectra can be used to determine the properties, characteristics and structure of a molecule of interest using the study of the chemical shifts of the molecule. The technique is known by those skilled in the art and can be utilized using 200, 300, 400, 500, 600, 800, 900 MHz NMR instruments, for example. In some embodiments herein, the polysaccharides are analyzed for their acetylation content using NMR spectroscopic techniques.

"Pharmaceutical excipient" as described herein refers to a substance formulated alongside the active ingredient of a medication. This can be included for the purpose of long-term stabilization, bulking up solid formulations that contain potent active ingredients (thus often referred to as "bulking agents", "fillers", or "diluents"), or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life. The selection of appropriate excipients also depends upon the route of administration and the dosage form, as well as the active ingredient and other factors.

"Immune disorder" as described herein, refers to a dysfunction of the immune system. Immune disorders can be "Primary immune deficiency diseases," which are those caused by inherited genetic mutations. Immune disorders can also be "Secondary or acquired immune deficiencies" which are caused by something outside the body such as a virus or immune suppressing drugs. Without being limiting, examples are systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease or Ataxia-telangiectasia. Immune disorders can be analyzed, for example, by examination of the profile of neural-specific autoantibodies or other biomarkers when detected in serum or cerebrospinal fluid in patients.

"Cytokines" as described herein, refers to small proteins that are important in cell signaling. Cytokine release has an effect on the behavior of cells around them. Cytokines are involved in autocrine signaling, paracrine signaling and endocrine signaling as immunomodulating agents, for example. Examples of anti-inflammatory cytokines can include but is not limited to interleukin (IL)-1 receptor antagonist, IL-4, IL-6, IL-10, IL-11, and IL-13.

DETAILED DESCRIPTION

Polysaccharides are one of the major constituents in *Aloe vera*. The major polysaccharide in *aloe* is glucomannan which consists of mannose and glucose with a 1, 4-β-linked backbone, where the mannose is predominant. The hydroxyl groups of mannose moieties may be substituted with acetyl groups and the *aloe* polysaccharides are referred to as acetylated glucomannan or interchangeably as Acemannan. Acemannan was a trade name which is used frequently in literature. Acetylated glucomannan is reported to be responsible for a variety of the biological activities of *Aloe vera* including immunostimulatory, anti-inflammatory, hypoglycemic, hypolipidemic, antibacterial, antiviral, and antitumor effects.

The positions of the acetylated groups found on the mannose moieties are 2-, 3-, or 6-acetyl, 2, 3-; 2, 6-; or, 3, 6-diacetyl, and 2, 3, 6-triacetyl substitutions, respectively. The reported acetyl contents found in native acetylated glucomannan were 15-26% acetylation in *aloe vera*.

The *aloe* leaf comprises an outer green rind and an inner clear gel. Both the outer green rind and inner gel contain polysaccharides. In the *aloe* manufacturing process, based on the plant parts to be used, *aloe* leaf products can be made from the entire leaf extract using the outer green rind and gel (termed 100×) or the extract using the inner gel only (termed 200×). During the *aloe* product manufacturing process enzymes and/or heat are applied to the plant parts. Both enzymes and heat can deacetylate the polysaccharides leading to the reduction of acetyl groups on the polysaccharides. Therefore, when polysaccharides undergo a manufacturing process, the content of acetyl groups is usually less than their native precursors. To recover or increase the content of the acetyl groups, which were lost during the manufacturing process, acetylating agents are used in a reaction with glucomannan to synthesize highly acetylated polysaccharides.

Described in the embodiments herein, *aloe* powder, which was used as the reaction starting material, which was first purified by ethanol precipitation. The ethanol undissolved polysaccharides were filtered and separated from ethanol soluble molecules to give crude *aloe* polysaccharides. The crude polysaccharides were then dissolved in water and dialyzed in a container filled with purified water. Water was frequently replaced with fresh water until the dialysis process was completed. The dialysates were centrifuged and then freeze dried to yield enriched acetylated glucomannan at the purity of 70%-90% by weight.

The acetylating agent, acetic anhydride $(CH_3CO)_2O$, was employed to prepare highly acetylated glucomannan. Acetyl chloride and acetic acid can also be used as acetylating agent. Either crude or enriched polysaccharides were treated with acetic anhydride and the reaction products were purified through dialysis to remove unreacted acetylating agent, catalyst, such as pyridine, sodium hydroxide, potassium hydroxide, sodium carbonate, or potassium carbonate and solvent. The purified reaction product was subjected to spectroscopic and chemical analysis to determine the contents of the polysaccharides and acetyl groups.

Infrared spectroscopic (IR) and nuclear magnetic resonance (NMR) spectroscopic methods were used in the identification and quantification of the reaction starting materials and products.

In some embodiments, a patient is identified to receive a therapeutic for inflammation after being diagnosed with inflammation by a physician. In some embodiments, the inflammation presents as one or more of heat, pain, redness, swelling, and loss of function of the skin or internal organs. In some embodiments, a patient is identified to receive a therapeutic for an immune disorder after being diagnosed with an immune disorder by a physician. In some embodiments, inhibition of the inflammatory response is measured by monitoring anti-inflammatory cytokines in a patient selected from a group consisting of interleukin (IL)-1 receptor antagonist, IL-4, IL-6, IL-10, IL-11, and IL-13. In some embodiments, a patient is identified to receive a therapeutic for cancer after being diagnosed with cancer by a physician. In some embodiments, tumor growth is measured and evaluated by monitoring the size of the tumor with one or more of the following techniques: computed tomography, magnetic resonance imaging (MRI), x-ray, mammography, ultrasound, and positive emission tomography (PET).

Materials and Methods

*Aloe* leaf juice powder (200× or 100×) was purchased from either Hainan Aloecorp Co., Ltd. (Hainan, China) or Pharmachem Laboratories, Inc., Improve USA (Anaheim, Calif., USA). Anhydrous ethanol and dimethyl sulfoxide (DMSO) were purchased from Sinopharm Chemical Reagent Co., Ltd (Shanghai, China). The dialysis membrane was purchased from Shanghai Yuanye Biological technology Co., Ltd (Shanghai, China). Acetic anhydride was purchased from Chengdu Kelong Chemical Reagent Inc. (Chengdu, China). Pyridine was purchased from China Shanghai Reagent Factory (Shanghai, China). All the reagents and chemicals were used without further purification. Fourier transform infrared spectroscopy was carried out on a PerkinElmer Frontier FT-IR Spectrometer (PerkinElmer Instruments, Norwalk, Conn., USA). $^1$H NMR (400 MHz) and $^{13}$C NMR (100 MHz) spectra were recorded on Bruker Ultrashield 400 Plus or Bruker 400 Avance III instrument (Fremont, Calif., USA) with $D_2O$ as solvent (Sigma-Aldrich, St. Louis, Mont., USA). Chemical shifts are reported in parts per million (ppm, δ). The quantitation of acetyl groups by $^1$H NMR was performed by weighing about 2-10 mg of samples and 5 mg of internal standard nicotinamide (Sigma-Aldrich, St. Louis, Mont., USA). Both samples and nicotinamide were dissolved in 1 mL of D$_2$O and incubated at 4° C. for 24 h before NMR analysis. The $^1$H-$^{13}$C correlation spectra were obtained by Heteronuclear Single Quantum Coherence (HSQC) spectra using standard gradient pulse sequences of Bruker Topspin software and performed on PABBO BB-1H/D Z-GRD probe. The molecular weight of polysaccharides were determined on a size exclusion chromatography (SEC) used PolySep-GFC-P-Linear column (300×7.5 mm) (Phenomenex, Inc., Torrance, Calif., USA) equipped with a TSKgel PWXL guard column (40×6 mm) (Sigma-Aldrich). The mobile phase was 0.1 M NaCl that was pre-filtered through a 0.22 µm GSWP membrane (Merck Millipore, Darmstadt Germany) before use. During analysis the mobile phase was further passed through an inline filter (0.10 µm×25 mm Durapore membrane filter, Millipore Co., Bedford, Mass.) before reaching to SEC column. The flow rate was 0.7 mL/min, the injection volume 100 µL, and column chromatography was carried out at 35° C. Samples were initially dissolved in 0.1 M NaCl at a concentration of 0.25-2 mg/mL, allowed to swell for 20-24 hours at 4° C., and then filtered through 0.45 µm MCE filter prior to injection. The light scattering measurement used Dawn Enhanced Optical System (DAWN HELEOS II) MALS detector equipped with 100 mW 662 nm Ga/As laser and 18 angle research grade light scattering photometer (Wyatt Technology Co, Santa Barbara, Calif., USA). The chromatographic system was consisted of a 2690 Separation Module with Waters 2410 differential refractometer (Waters Corp, Milford, Mass., USA). The instrument was certified by the manufacturer using polystyrene 200 kDa in toluene for MALS detector and bovine serum albumin (BSA) 66,000 Da for MALS/RI detectors. The SEC/MALS/RI detectors were connected in series. The inter detector delay was determined as 255.6 µL, using BSA. Data from the light scattering and the differential refractometers were analyzed using Wyatt ASTRA 6.1.5.22 software. A refractive index increment (dn/dc) of 0.14 mL/g was used during the entire experiment. The data obtained from MALS measurement was processed using the Zimm extrapolation method. For the sample MW and MWD analysis by SEC/RI system calibrated with pullulan or dextran standards, the calibration curves were obtained by plotting the logarithm of molecular weight versus retention time and a linear regression for narrow polydispersity pullulans and third-order polynomial fit for broad polydispersity dextrans were performed using the Empower 3 GPC/SEC software (Waters Corp, Milford, Mass., USA). For pullulan calibration combined with broad polydispersity *aloe* polysaccharides, third-order polynomial fit was used.

Embodiment 1

Preparation of Acetylated Polysaccharides from Crude *Aloe* Polysaccharides

A total of 100 grams of 200×*aloe* leaf juice powder was dissolved in 900 milliliters of water to make a 10% *aloe* solution. To the 10% *aloe* solution, 3,600 milliliters of ethanol was added slowly with stirring and the ethanol solution was placed at 4° C. for 18 hours. A white precipitate was formed in the ethanol solution and the precipitate was obtained through a filtration system. The precipitate was rinsed with 250 mL of ethanol twice and freeze dried to yield 39 grams of crude polysaccharides, 83008-175-15 (1).

A total of 500 milligrams of 83008-175-15 (1) was placed into a 100-mL round bottle flask and 40 milliliters of DMSO was added. After the DMSO solution was stirred at room temperature for 24 hours, 3 milliliters of pyridine and 2.5 milliliters of acetic anhydride were sequentially introduced into the DMSO solution. The reaction shown below took place under the conditions of stirring in an ice water bath for 30 minutes. The reaction solution was then allowed to warm to room temperature for 1.5 hours. After 2 hours, water was added into the reaction product and the solution was transferred into a dialysis membrane tube with molecular weight cut-off (MWCO) 8,000-14,000 Da. The reaction product was dialyzed until the scent of pyridine was removed. The dialysate was freeze dried to yield white acetylated polysaccharides 83018-3-3 at a total weight of 47 milligrams of the product with 86% purity by weight (2).

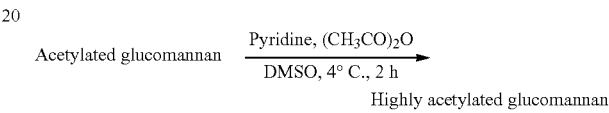

Figure 2A:
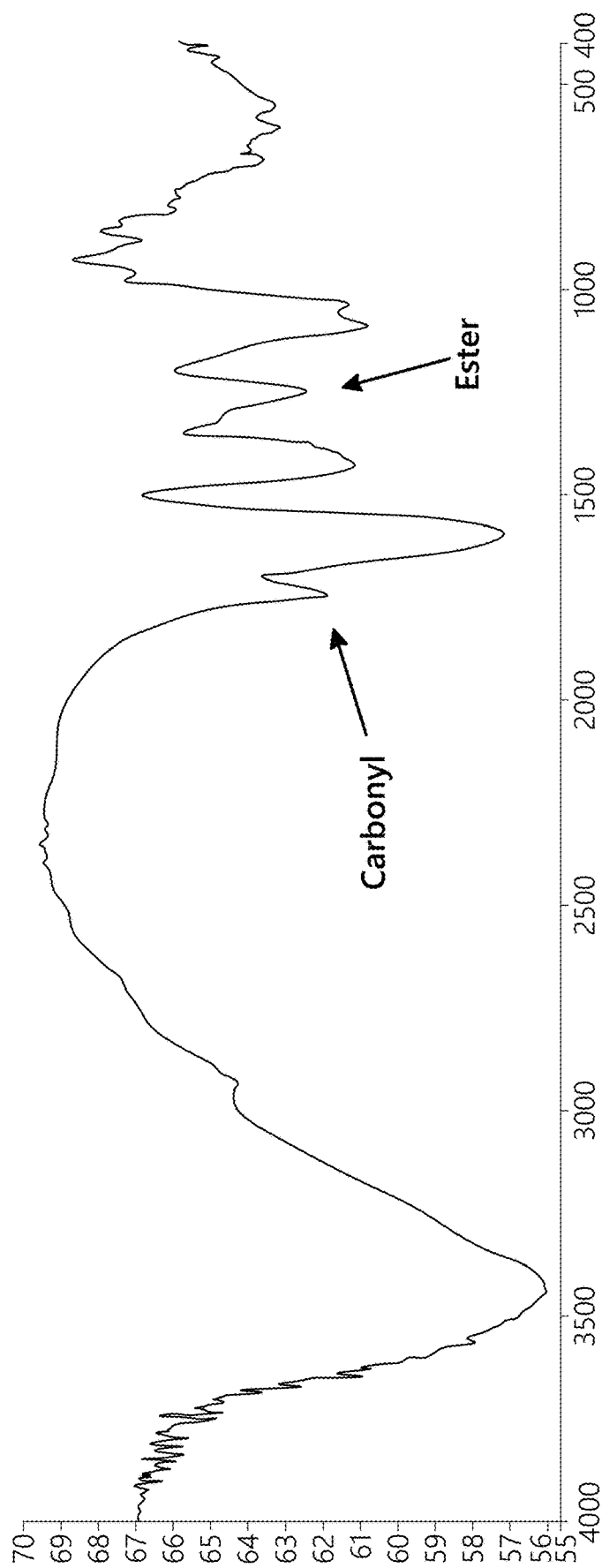
FIG. 2A shows the IR spectrum of crude polysaccharides, 83008-175-15 (1)
Figure 2B:
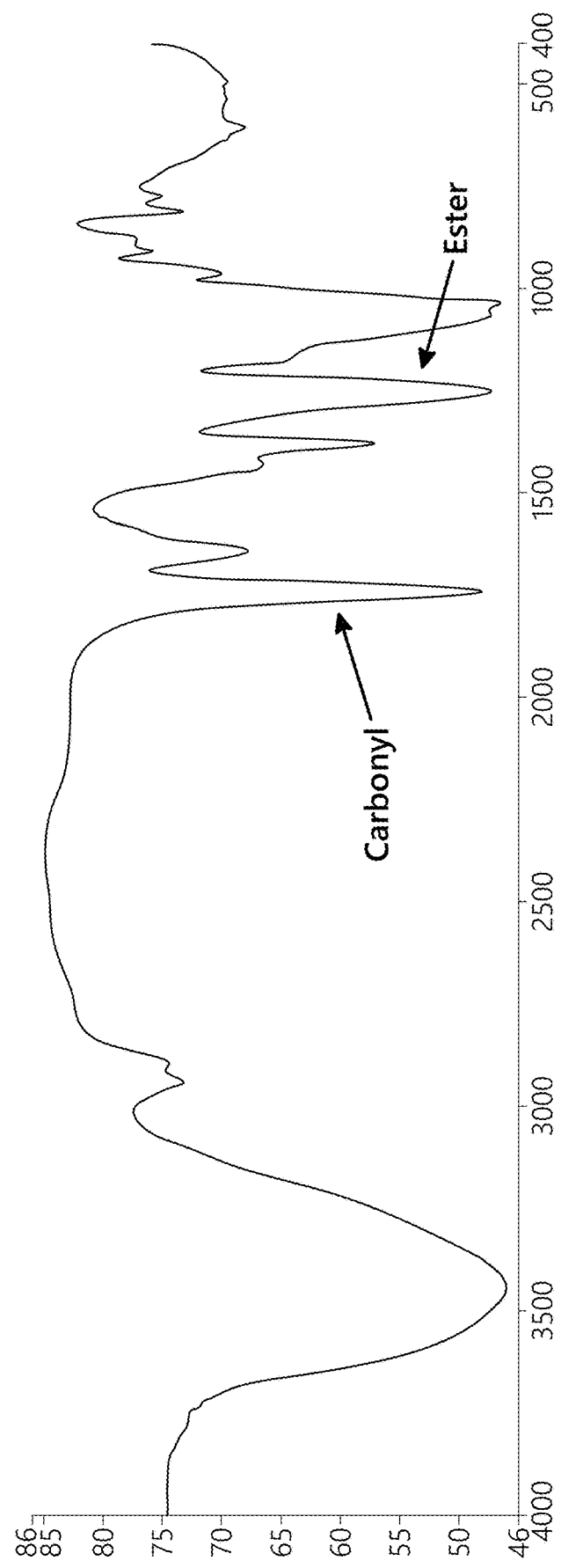
FIG. 2B shows the IR spectrum of acetylated product 83018-3-3 (2) from the crude polysaccharides 83008-175-15 (1).

The acetylated product (2) was analyzed by infrared spectroscopy (IR), where the stretch bond of the carbonyl group (=O) at ~1741 cm$^{-1}$ and ester group (—O—) at ~1247 cm$^{-1}$ were shown to be stronger in the acetylated product (2) than those in the crude polysaccharides (1) (FIGS. 2A and 2B), indicating that there were more acetyl groups in the aceylated product (2) and indicated that the acetylation had taken place. The reaction led to the surprising result of obtaining higher acetylation than the plant process of acetylation through this reaction.

Figure 3:
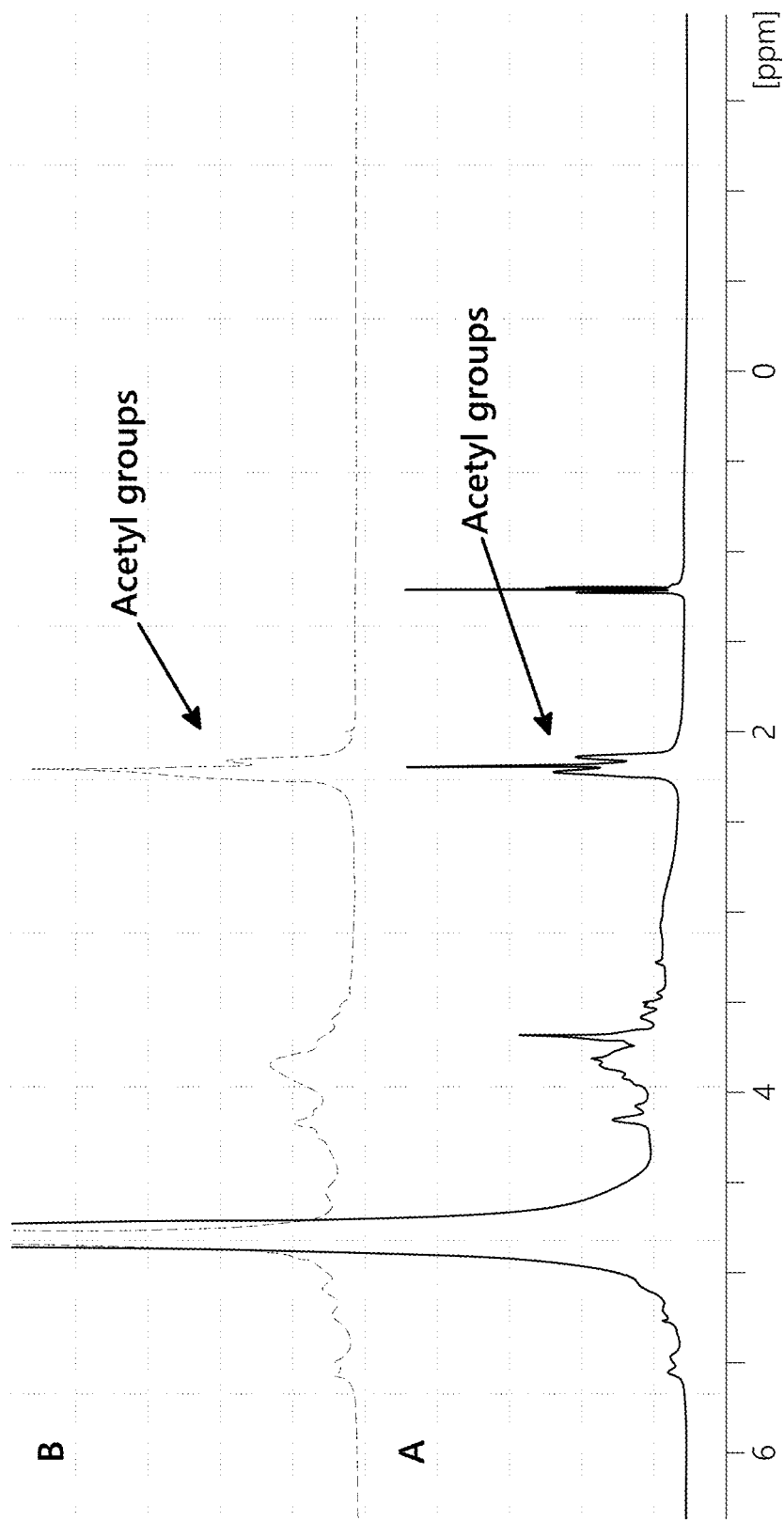
FIG. 3 shows the $^1$H NMR spectra of A) crude polysaccharides, 83008-175-15 (1); B) acetylated product 83018-3-3 (2) from the crude polysaccharides.

In the $^1$H NMR spectra, the acetyl groups appeared at 2.0-2.2 ppm and were quantitated. It was shown through $^1$H NMR that the polysaccharides yielded 7.5% acetylation in the crude polysaccharides (1) and 17.8% in the acetylated product (2), respectively, which further confirmed the acetylation of 2 (FIG. 3). Overall the sample showed multiple acetylated hydroxyl groups of sugars.

Embodiment 2

Preparation of Acetylated Polysaccharides from Enriched Polysaccharides

The ethanol undissolved crude polysaccharides, 83008-175-15 (1) was dialyzed in a membrane tube with MWCO 8,000-14,000 Da to yield enriched polysaccharides 83018-7-11 (3). Polysaccharide 3 was then treated by acetic anhydride-pyridine as in the same conditions used in Embodiment 1 to yield acetylated product, 83018-9-21, (4). The product 4 was purified through dialysis with a molecular weight cut off (MWCO) membrane of 8,000-14,000 Da and freeze dried to give rise to white powder.

Figure 4A:
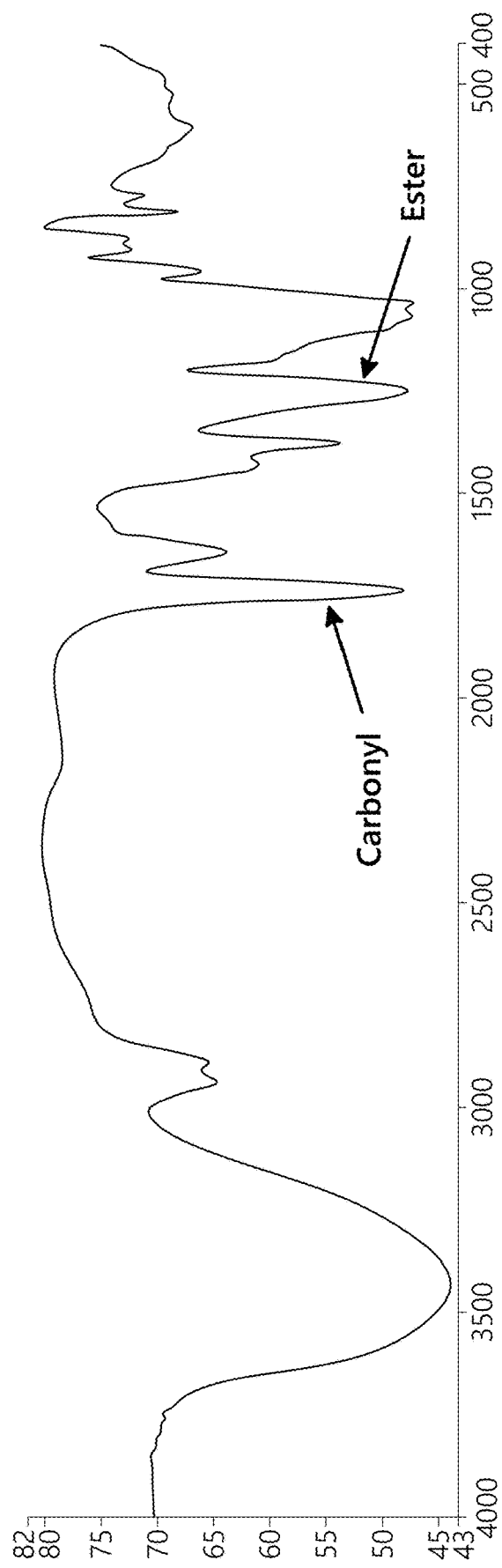
FIG. 4A shows the IR spectrum of enriched polysaccharides, 83018-7-11 (3)
Figure 4B:
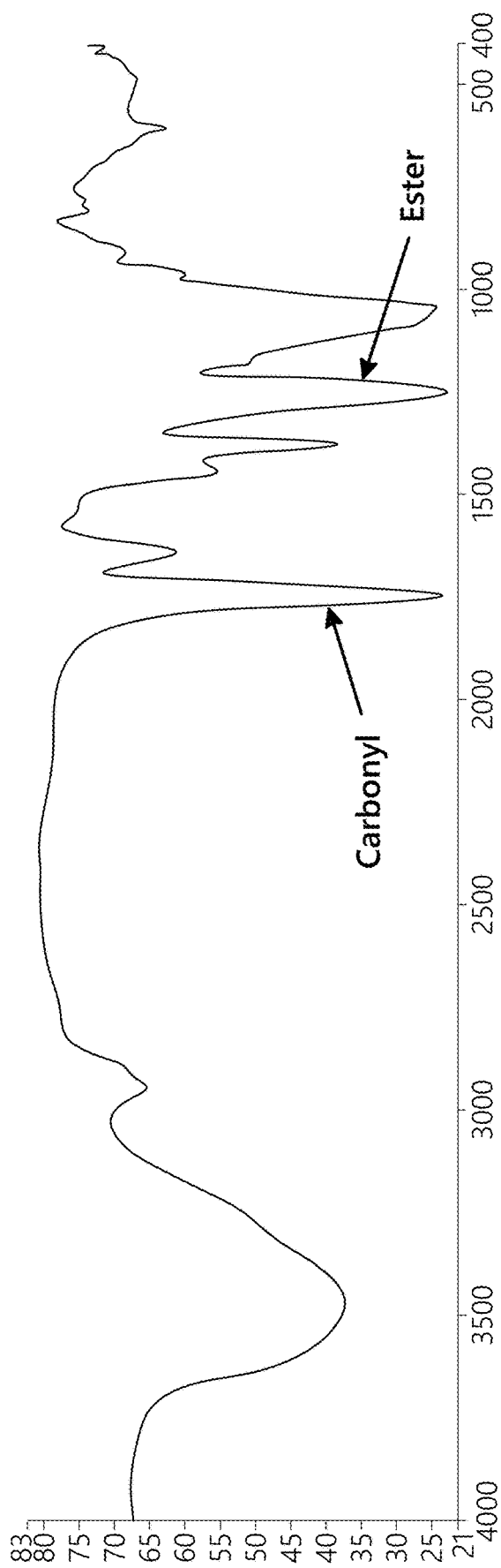
FIG. 4B shows the IR spectrum of acetylated product 83018-9-21 (4) from the enriched polysaccharides 83018-7-11 (3).
Figure 5:
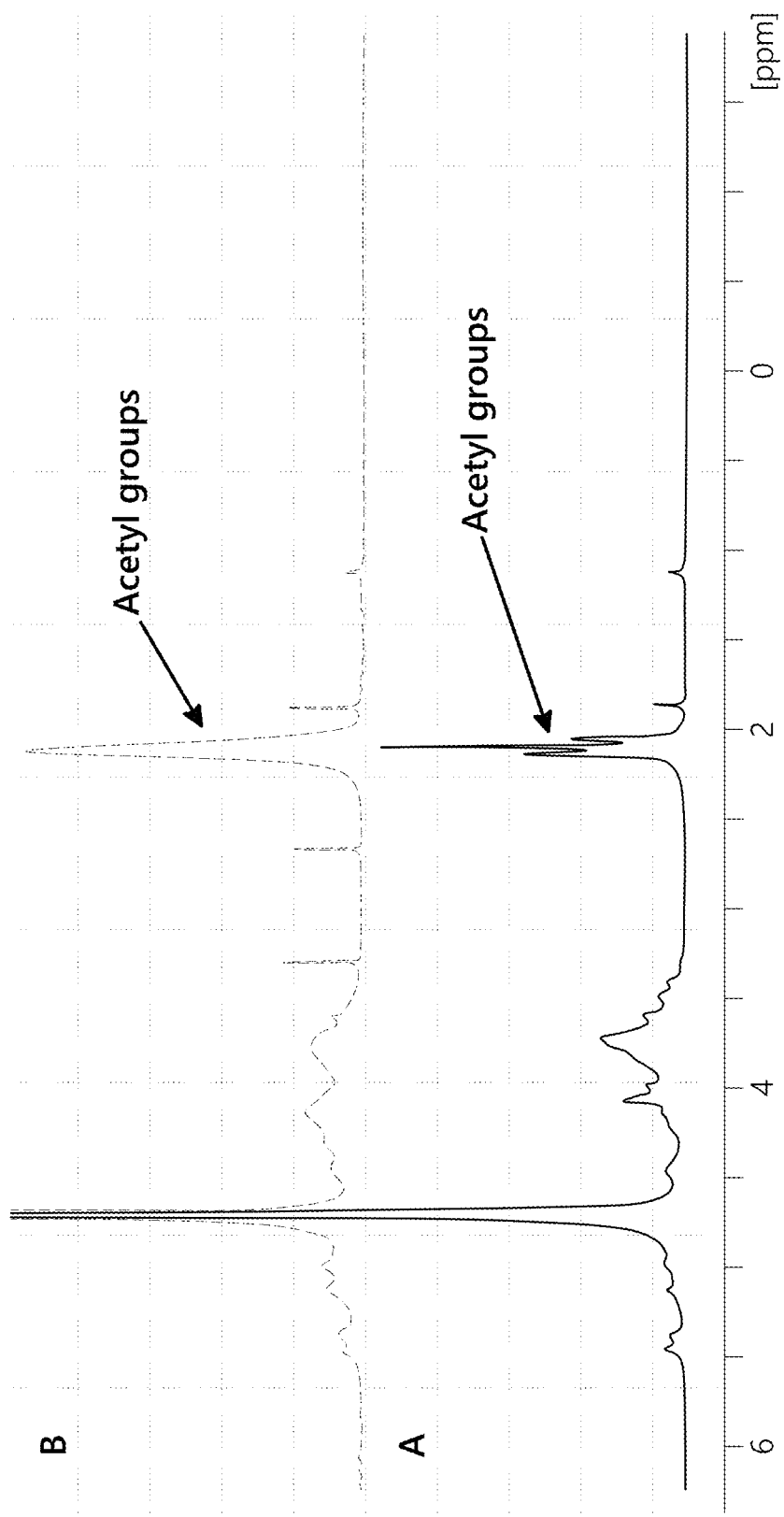
FIG. 5 shows the $^1$H NMR spectra of A) enriched polysaccharides, 83018-7-11 (3); B) acetylated product 83018-9-21 (4) from the enriched polysaccharides.

Polysaccharides 4 showed the stronger carbonyl signal around 1742 cm$^{-1}$ and ester signal around 1244 cm$^{-1}$ than those of polysaccharide 3 in IR spectra (FIGS. 4A and 4B). In the analysis of $^1$H NMR spectra (FIG. 5), the contents of acetyl groups of polysaccharide 3 and polysaccharides 4 were 17.2% and 24.5%, respectively, indicating the successful acetylation as shown in the polysaccharide product, 4. As such, the acetylation reaction surprisingly yielded a high percentage of acetylated product as compared to the crude polysaccharides.

Figure 6:
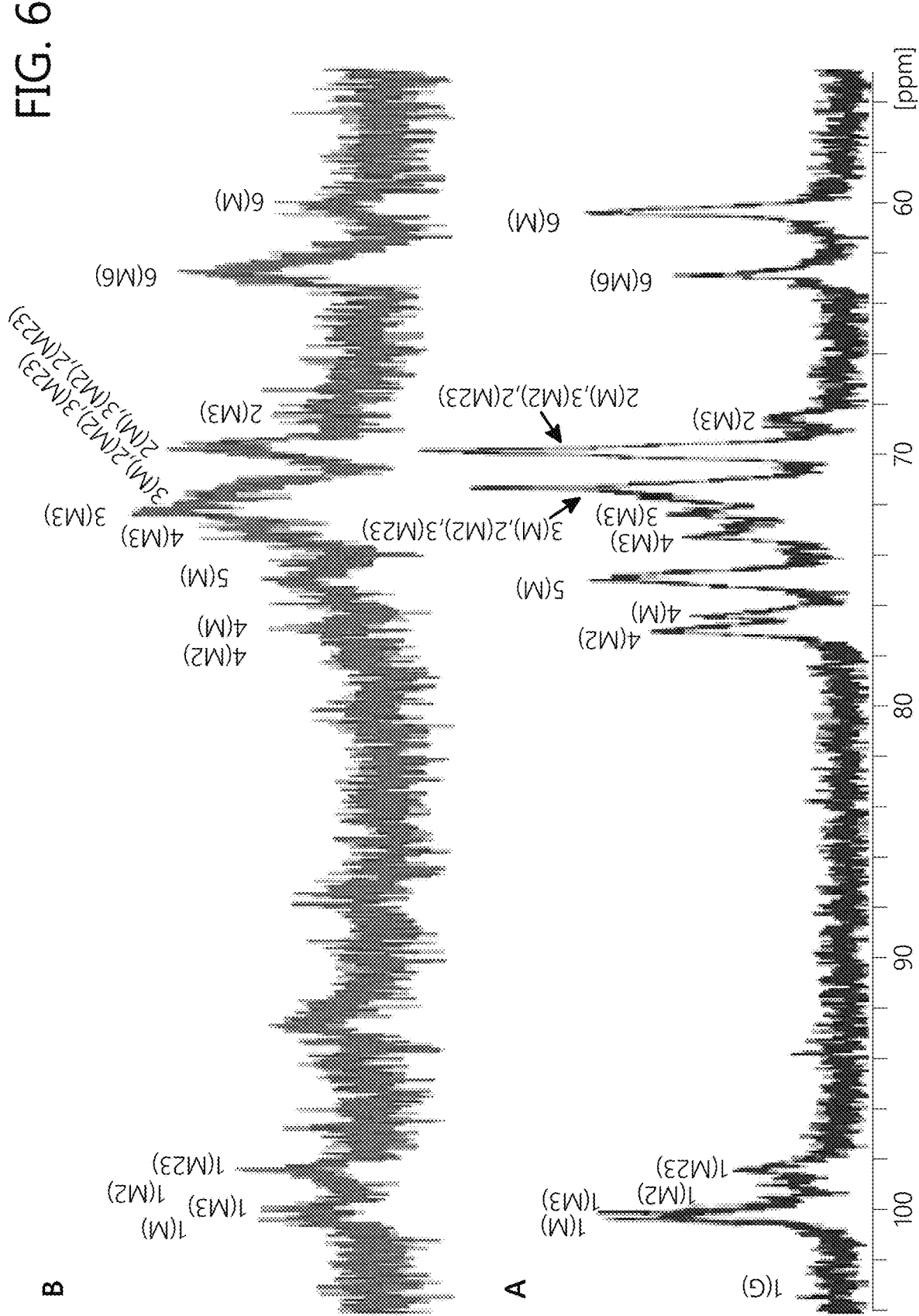
FIG. 6 shows the Carbon-13 spectra of A) enriched polysaccharides, 83018-7-11 (3); B) acetylated product 83018-9-21 (4) from the enriched polysaccharides. 6M: C-6 of mannopyranosyl; 6M6: C-6 of 6-acetyl mannopyranosyl; 3M23: C-3 of 2,3-diacetyl mannopyranosyl.

Comparing the $^{13}$C NMR of polysaccharides 3 and polysaccharides 4, the signals corresponding to acetyl groups were increased (See FIG. 6). For example, the signal at 60.3 ppm is from C-6 and downfield shift to 63.5 ppm when 6-O was substituted by acetyl group. The signal intensity at 60.3 ppm is higher than that of 63.5 ppm in 3, suggesting fewer acetyl groups at 6-OH of 3. In polysaccharides 4, however, the intensity from the acetylate C-6 was significantly higher than its non-acetylated C-6. Similarly, the signals arising from C-2 and C-3 due to the acetylations on O-2 and O-3 around 72-74 ppm were increased, too (FIG. 6).

Figure 7:
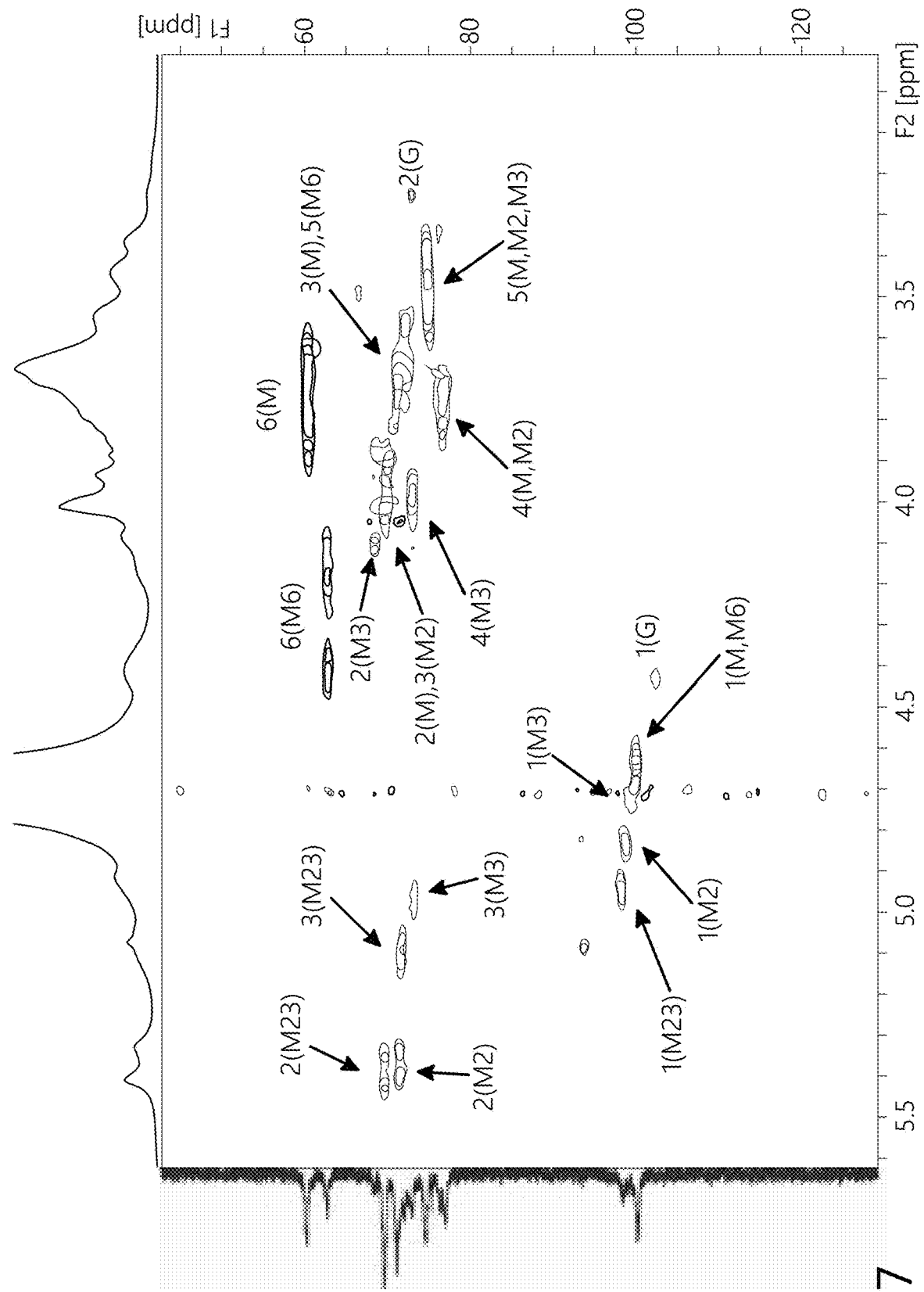
FIG. 7 shows the HSQC spectrum of enriched polysaccharides, 83018-7-11 (3); HSQC is used to correlate directly C-H coupled nuclei. In the contour plot, horizontal and vertical axes are proton and carbon chemical shifts, respectively. When proton is bonded to a carbon, a cross peak can be found at the intersection of the horizontal line from carbon signal and vertical line from proton signal.

Although $^{13}$C NMR spectra clearly exhibited the differences of the polysaccharides before and after acetylation, because of their low sensitivity and resolution here, the 2D HSQC (Heteronuclear Single Quantum Coherence) spectra were acquired on polysaccharides 3 and polysaccharides 4. In the HSQC spectrum of polysaccharide 3, a characteristic cross-peak from the proton-carbon correlation at 5.35, 5.42/69.7 is shown that corresponds to the signal of the C-2 due to the substitution of acetyl groups on the both of O-2 and O-3 position and designated 2M23 (M representing mannopyranosyl moiety). The cross-peaks at 5.10/71.7, 5.34, 5.40/71.6, and 4.78/73.1 resulted from the signals of C-3 due to 2,3-O-diacetyl (3M23), C-2 due to 2-O-acetyl (2M2), and C-3 due to 3-O-acetyl (3M3) substitutions, respectively. The cross-peak at 3.55, 3.78/60.3 is assigned to be the signal of C-6 (6M), the non-acetyl substituted 6-O position, while the 6-acetylated proton-carbon cross peak is found at 4.19, 4.28/63.5 (6M6). The assignments of the other cross-peaks are shown in FIG. 7.

Figure 8:
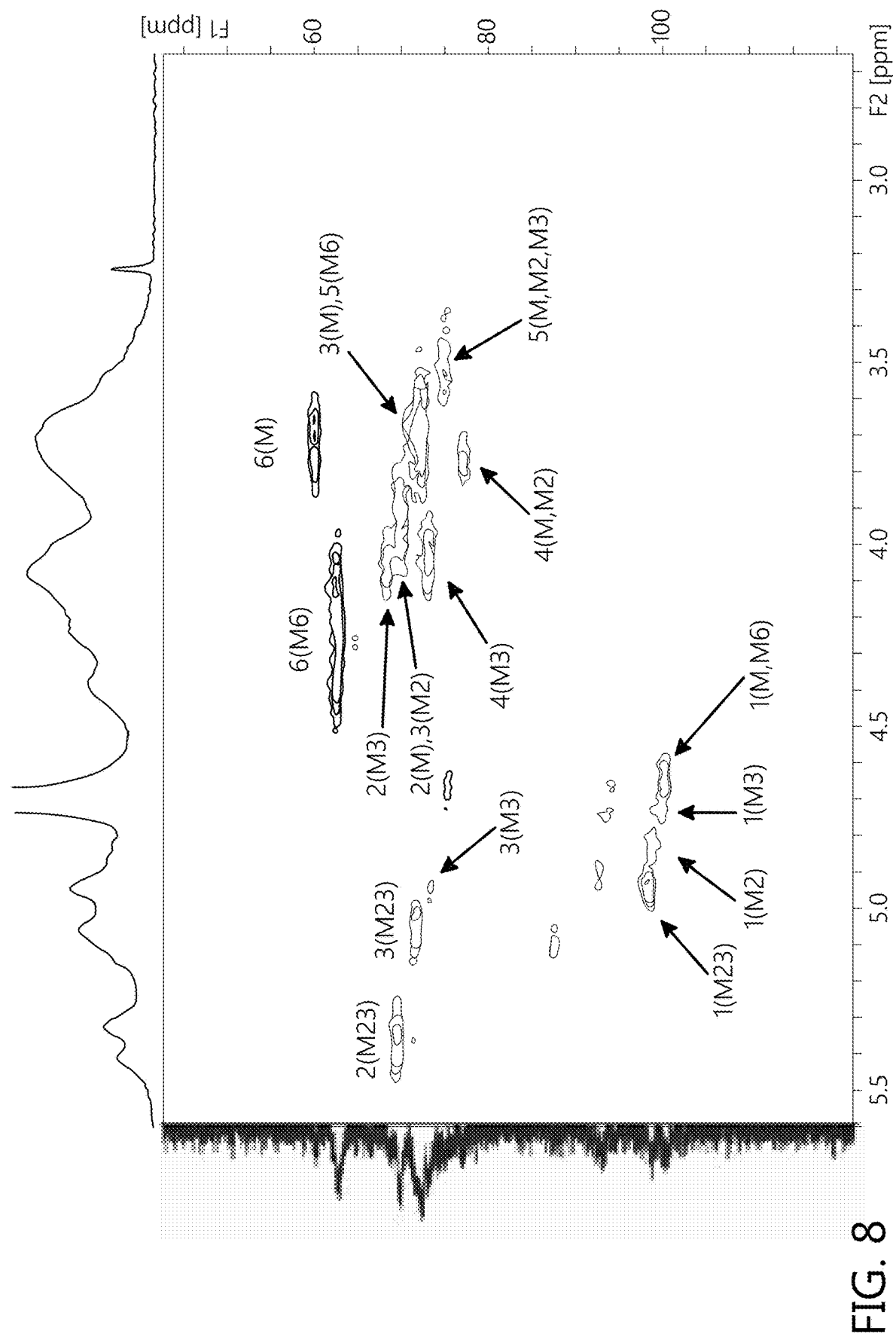
FIG. 8 shows the HSQC spectrum of enriched polysaccharides, 83018-9-21 (4).
Figure 9A:
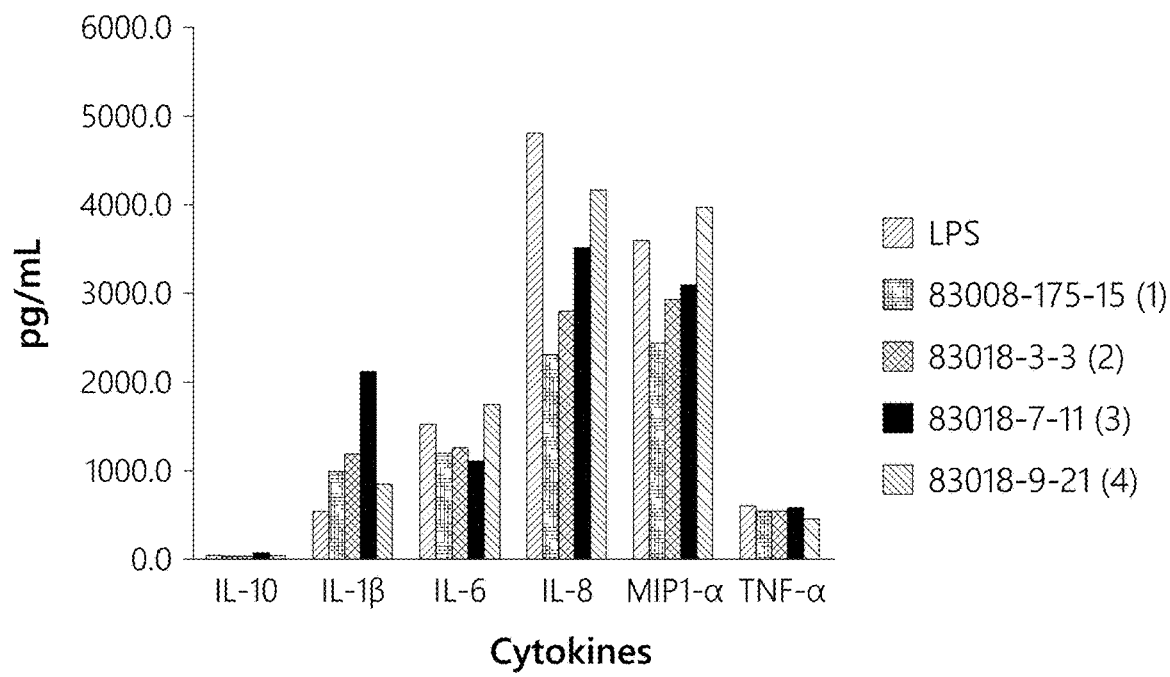
FIG. 9A shows that acetylated polysaccharides decrease anti-inflammatory activity. This figure shows the effect of 1-4 on of cytokines IL-1β, IL-6, IL-8, IL-10, MIP-1α, and TNFα.
Figure 9B:
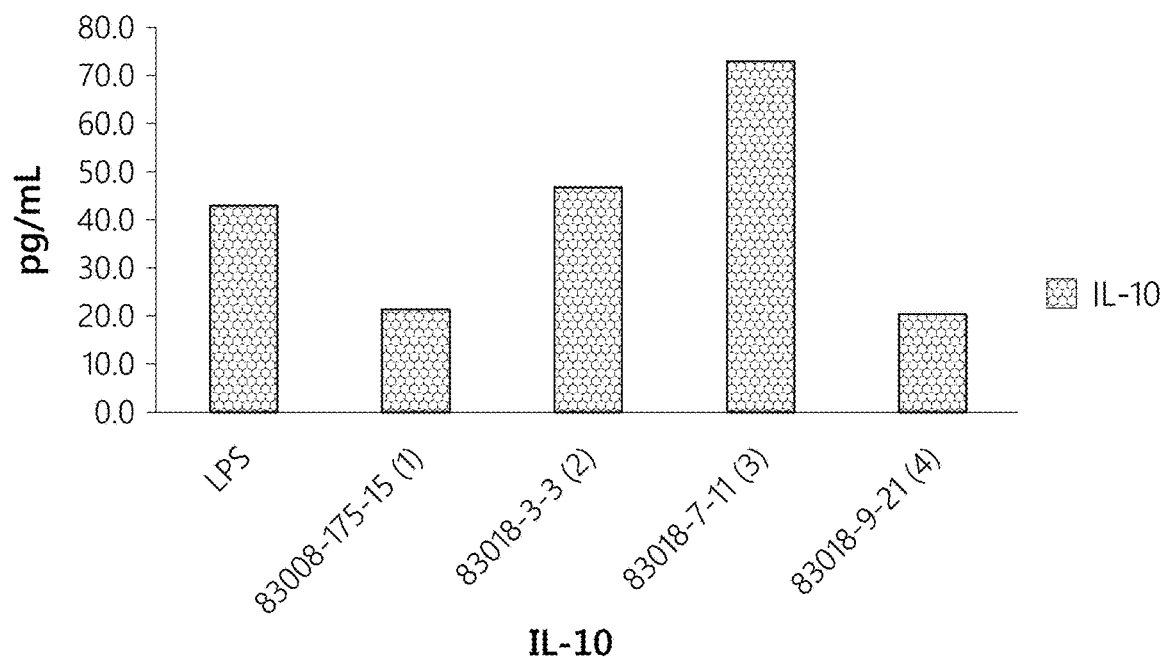
FIG. 9B shows the effect of 1-4 on of cytokines IL-10.

Comparing the HSQC spectrum of polysaccharide 4 (FIG. 8) to that of polysaccharide 3, the cross-peaks due to the signals from C-2 of the 2-O-acetyl (2M2) and C-3 of the 3-O-acetyl (3M3) substitution turned to weak cross-peaks or the cross-peaks disappeared, while the cross-peaks at 5.34, 5.41/69.5 resulted from the signals of C2 (2M23) and 5.10/71.8 due to C-3 (3M23) of the 2,3-O-diacetyl substitution became predominant, respectively. Similarly, the signal intensity of 6-acetylated cross-peak at 4.16, 4.37/62.6 (6M6) in 4 is stronger than the non-acetylated signal at 3.69, 3.79/60.1 (6M), while opposite is observed in polysaccharide 3 of the 6M6 and 6M. All these results indicate that the more acetyl groups are existed in polysaccharide 4 than polysaccharide 3, confirming that polysaccharide 4 is the acetylated product of polysaccharide 3.

Acetylation was performed in the same way as described above on the processed *aloe* polysaccharides 100×(033694-3500PS, 6), inner gel 200×(030604-3500PS, 9), and 100×(032889-3500PS, 12) to give rise to three acetylated polysaccharides 7 (83018-51-22), 10 (83018-51-20), and 13 (83018-16-16), respectively. NMR analysis confirmed that the polysaccharides 7, 10, and 13 are the acetylated of its precursor polysaccharides 6, 9, and 12, respectively. The contents of acetylated groups determined by proton NMR before and after acetylation are shown in Table 1.

TABLE 1

Contents of acetylated groups of the polysaccharides before and after acetylation.

| Acetyl Groups (weight %) | | Increment of Acetyl |
|---|---|---|
| Before acetylation | After acetylation | Group (%) |
| 83008-175-15, 1   7.5% | 83018-3-3, 2   17.8% | 137% |
| 83018-7-11, 3   17.2% | 83018-9-21, 4   24.5% | 42% |

TABLE 1-continued

Contents of acetylated groups of the polysaccharides before and after acetylation.

| Acetyl Groups (weight %) | | Increment of Acetyl |
|---|---|---|
| Before acetylation | After acetylation | Group (%) |
| 033694-3500PS, 6   12.1% | 83018-51-22, 7   20.3% | 68% |
| 030604-3500PS, 9   13.5% | 83018-51-20, 10   19.7% | 46% |
| 032889-3500PS, 12   11.6% | 83018-16-16, 13   20.2% | 74% |

Analysis of Polysaccharide Molecular Weight

Decrease of molecular weights after acetylation was found (Table 2). Theoretically, the molecular weight of acetylated polysaccharides should be increased because of adding more acetyl groups. The reason of decreasing is probably that the acetylation breaks the network of the inter-polysaccharides due to the hydrogen bonds. The formation of acetyl bonds, make the numbers of the hydroxyl groups less available for hydrogen bonds.

TABLE 2

Molecular weight of polysaccharides before and after acetylation
Molecular weight (kilodaltons)

| Before acetylation | | After acetylation | |
|---|---|---|---|
| 3 | 162 | 4 | 18 |
| 9 | 80 | 10 | 29 |

Embodiment 5

Immunomodulatory Activity of Acetylated Polysaccharides

As in Table 3, non-acetylated *aloe* preparation of inner gel 030604-3500PS, 9, showed an immune modulatory activity in that its treatment of PBMC in the presence of LPS led to a significant decrease in pro-inflammatory cytokines (IL-1β and IL-6) and to a significant increase in anti-inflammatory IL-10, as compared to their levels of expression stimulated by LPS. Interestingly, acetylation of this preparation 83018-51-20, 10, which increased acetylated polysaccharides from 13.5% to 19.7% (an increment of 46%) led to a significant reduction of proinflammatory IL-1β and TNF-α, indicating that an increase in acetylation of this particular *aloe* preparation caused a change in its immune modulatory activity. On the other hand, non-acetylated *aloe* gel powder (200×), 3, showed an immune modulatory activity in that its treatment of PBMC in the presence of LPS led to a significant decrease in IL-6, TNF-α, and IFN-γ and to a significant increase in IL-10, as compared to their levels of expression stimulated by LPS. Acetylation of this preparation, 4, which increased acetylated polysaccharides from 14.2% to 24.5% (an increment of 42%) led to a significant increase in IL-10 but to insignificant change in the proinflammatory cytokines, indicating that an increase in acetylation of this particular *aloe* preparation caused a change in its immune modulatory activity. The results suggest that an increase in acetylation of the tested *aloe* preparations caused a significant alteration of their immune modulatory activity.

TABLE 3

Contents of acetylated groups of the polysaccharides and effect on cytokine expression from human PBMCs

| Samples No. | Cytokines Affected (+, up/−, down) |
|---|---|
| Inner gel (200X), 030604-3500PS, 9 | IL-1β (+), IL-6 (+), IL-10 (+) |
| Inner gel 200X Acetylation, 83018-51-20, 10 | IL-1β (−), TNF-α (−) |
| Aloe gel powder (200X), 83018-7-11, 3 | IL-6 (−), IL-10 (+), TNF-α (−), IFN-γ (−) |
| Aloe gel powder (200X) Acetylation, 83018-9-21, 4 | IL-10 (+) |

Embodiment 6

Acetylation of Crude Polysaccharides, 83018-3-3 (2)

A 500 milligram sample of crude polysaccharides 83008-175-15 (1) was accurately weighed into a 50 milliliter round bottom flask and 40 milliliters of DMSO was added. After the solution was stirred at ambient temperature for 24 hours, 3 milliliters of pyridine and 2.5 mL of acetic anhydride were successively added with stirring in an ice water bath for 30 min and then allowed warm to room temperature for 1.5 h. After 2 hours, the reaction was quenched by adding 20 mL of water. The reaction product was transferred into a dialysis membrane tube with MWCO 8,000-14,000 Da until no pyridine was smelled. The dialysate was lyophilized to yield 47 mg of white acetylated polysaccharides 83018-3-3 (2). IR (KBr) vmax.: 3437, 1741, 1638, 1376, 1247, 1037 cm$^{-1}$. $^1$H NMR (400 MHz, D$_2$O) δ (ppm): 2.01-2.20 (br., m, —COCH$_3$); $^{13}$C NMR (100 MHz, D$_2$O) δ (ppm) 100.2 (C-1M), 99.6 (C-1M3), 98.7 (C-1M2), 98.4 (C-1M23), 76.9 (C-4M), 75.0 (C-5M), 73.3 (C-3M3), 71.8 (C-3M23), 71.4 (C-3M, C-2M2), 69.8 (C-2M), 69.5 (C-2M23), 68.4 (C-2M3), 62.8 (C-6M6), and 60.3 (C-6M). The contents of acetyl groups are 17.8%.

Embodiment 7

Acetylation of Enriched Polysaccharides, 83018-9-21 (4)

A 500 milligrams of enriched polysaccharides, 83018-7-11 (3) was accurately weighed into a 50 milliliter round bottom flask and 24 milliliters of DMSO was added. The solution was settled at ambient temperature for 24 hours and 1.8 milliliters of pyridine as well as 1.5 milliliters of acetic anhydride were successively added with stirring in an ice water bath for 30 min and then allowed warm to room temperature for 1.5 hours. After 2 hours, water was added to quench the reaction and the solution was transferred into a dialysis membrane tube with a MWCO of 8,000-14,000 Da. The reaction product was dialyzed until there was no scent of pyridine and the dialysate was lyophilized to yield a white enriched acetylated polysaccharide product, 83018-9-21 (4) at 362 milligrams. IR (KBr) vmax.: 3474, 1742, 1638, 1375, 1244, 1043 cm$^{-1}$. $^1$H NMR (400 MHz, D$_2$O) δ (ppm): 1.98-2.22 (br., m, —COCH$_3$); $^{13}$C NMR (100 MHz, D$_2$O) δ (ppm): 100.2 (C-1M), 99.5 (C-1M3), 99.8 (C-1M2), 98.3 (C-1M23), 77.0 (C-4M), 75.0 (C-5M), 73.4 (C-4M2), 73.3 (C-3M, C-3M3), 71.8 (C-3M23), 69.7 (C-3M), 69.5 (C-2M23), 68.6 ( ) 62.6 (C-6M6), and 60.0 (C-6M). The contents of acetyl groups are 24.5%.

Embodiment 8

General Process for Preparation of Crude Polysaccharides 033694 AIRs

A total of 50 grams of *Aloe* leaf juice powder (100×, 033694) was accurately weighed into a 1 L glass breaker and 450 milliliters of water was added. The solution was sonicated until the *aloe* powder was completely dissolved and then was slowly poured into 1800 milliliters of anhydrous ethanol under stirring. The alcohol solution was placed in a refrigerator at 4° C. overnight. A white precipitate was obtained by filtration through a filter paper under vacuum and washed with 25 milliliters of 80% ethanol alcohol After the 25 milliliters of 80% ethanol alcohol washing solution was removed, repeated washing by adding another 25 milliliters of 80% ethanol alcohol. The precipitate was dried in vacuum and a total of 27 grams of crude polysaccharide 033694 AIRs (5) was obtained. IR (KBr) vmax: 3376, 1591, 1420, 1259, and 1093 cm$^{-1}$. $^1$H NMR (400 MHz, D$_2$O) δ (ppm): 2.03-2.17 (br., m, —COCH$_3$). The contents of acetyl groups are 2.6%.

Embodiment 9

Preparation of Enriched Polysaccharides 100×-AIRs-3500DaPs (6)

A total of 2 grams of crude polysaccharide 033694 AIRs (5) was weighed and dissolved in about 100 milliliters of water and was dialyzed in a membrane tube with a MWCO 3500 Da for 2 days. During the dialysis, the solution was frequently replaced with fresh water until the process was completed. The dialysate was lyophilized to yield 202 milligrams of white enriched polysaccharides 100×-AIRs-3500 DaPs (6). IR (KBr) vmax.: 3412, 1737, 1629, 1376, 1248, and 1034 cm$^{-1}$. $^1$H NMR (400 MHz, D$_2$O): δ (ppm): 2.00-2.20 (br., m, —COCH$_3$). The contents of acetyl groups are 12.1%

Embodiment 10

Acetylation of Enriched Polysaccharides, 83018-51-22 (7)

A 500 mg of enriched polysaccharides, 100×-AIRs-3500 DaPs (6) was accurately weighed into a 50-mL round bottom flask and 40 mL of DMSO was added. The solution was settled at ambient temperature for 24 h and 3 mL of pyridine as well as 2.5 mL of acetic anhydride were successively added with stirring in an ice water bath for 30 min and then allowed to room temperature for 1.5 h. After 2 hours, water was added to quench the reaction and the solution was transferred into a dialysis membrane tube with 3500 Da. The reaction product was dialyzed until no pyridine was smelled and the dialysate was lyophilized to yield a white enriched acetylated polysaccharide product, 83018-51-22 (7) 430 mg. IR (KBr) vmax.: 3329, 1740, 1641, 1376, 1247, and 1042 cm$^{-1}$. $^1$H NMR (400 MHz, D$_2$O) δ (ppm): 1.99-2.24 (br., m, —COCH$_3$). The contents of acetyl groups are 20.3%.

Embodiment 11

General Process for Preparation of Crude Polysaccharides 030604 AIRs (8)

A total of 100 grams of *aloe* gel powder (200:1, 030604) was accurately weighed into a 1-L glass beaker and 900 mL of water was added. The solution was sonicated until the *aloe* powder was completely dissolved and then was slowly poured into 3600 mL of anhydrous ethanol alcohol under stirring. The alcohol solution was placed in a refrigerator at 4° C. overnight. A white precipitate was obtained by filtration through filter paper and washed with 50 mL of 80% alcohol for two times. The precipitate was dried in vacuum and a total of 41 g of crude polysaccharides 030604 AIRs (8) was obtained. IR (KBr) vmax: 3385, 1735, 1591, 1413, 1250, and 1091 cm$^{-1}$. $^1$H NMR (400 MHz, D$_2$O): δ (ppm): 2.01-2.17 (br., m, —COCH$_3$). The contents of acetyl groups are 3.6%.

Embodiment 12

Preparation of Enriched Polysaccharides 100×-030604-3500 DaPs (9)

A total of 2 g of crude polysaccharide 030604 AIRs (8) was weighed and dissolved in about 100 mL of water and then was dialyzed in membrane tube with MWCO 3500 Da for 2 days. During the dialysis, the solution was frequently replaced with fresh water until the process was completed. The dialysate was lyophilized to yield 405 mg of white enriched polysaccharides 100×-030604-3500 DaPs (9). IR (KBr) vmax.: 3420, 1740, 1644, 1376, 1246, and 1068 cm$^{-1}$. $^1$H NMR (400 MHz, D$_2$O) δ (ppm): 2.02-2.20 (br., m, —COCH$_3$). The contents of acetyl groups are 13.5%

Embodiment 13

Acetylation of Enriched Polysaccharides, 83018-51-20 (10)

A 300 milligram sample of enriched polysaccharides, 100×-030604-3500 DaPs (9) was accurately weighed into a 50-millieter round bottom flask and 24 mL of DMSO was added. The solution was settled at ambient temperature for 24 hours and 1.8 milliliters of pyridine as well as 1.5 mL of acetic anhydride were successively added with stirring in an ice water bath for 30 min and then allowed to room temperature for 1.5 h. After 2 hours, water was added to quench the reaction and the solution was transferred into a dialysis membrane tube with 3500 Da. The reaction product was dialyzed until no pyridine was smelled and the dialysate was lyophilized to yield a white enriched acetylated polysaccharide product, 83018-51-20 (10) 191 mg. IR (KBr) vmax.: 3440, 1741, 1638, 1376, 1246, and 1042 cm$^{-1}$. $^1$H NMR (400 MHz, D$_2$O) δ (ppm): 1.97-2.24 (br., m, —COCH$_3$). The contents of acetyl groups are 19.7%.

Embodiment 14

General Process for Preparation of Crude Polysaccharides 032889 AIRs (11)

A total of 100 g of *Aloe* leaf juice powder (100×, 032889) was accurately weighed into a 1 L of glass breaker and 900 mL of water was added. The solution was sonicated until the *aloe* powder was completely dissolved and then was slowly poured into 3600 mL of anhydrous ethanol alcohol under stirring. The alcohol solution was placed in a refrigerator at 4° C. overnight. A white precipitate was obtained by filtration and washed with 50 mL of 80% alcohol for two times. The precipitate was dried in vacuum and a total of 50 g of crude polysaccharides 032889 AIRs (11) was obtained. IR (KBr) vmax: 3374, 1591, 1418, 1254, and 1088 cm$^{-1}$; $^1$H NMR (400 MHz, D$_2$O) δ (ppm): 2.02-2.17 (br., m, —COCH$_3$). The contents of acetyl groups are 3.3%.

Embodiment 15

Preparation of Enriched Polysaccharides 100×-032889-3500 DaPs (12)

A total of 1 g of crude polysaccharide 032889 AIRs (11) was weighed and dissolved in 100 mL of water and then was dialyzed in membrane tube with MWCO 3500 Da for 2 days. During the dialysis, the solution was frequently replaced with fresh water until the process was completed. The dialysate was lyophilized to yield 126 mg of white enriched polysaccharides 100×-030604-3500 DaPs (12). IR (KBr) vmax.: 3401, 1739, 1634, 1376, 1248, and 1067 cm$^{-1}$. $^1$H NMR (400 MHz, D$_2$O) δ (ppm): 2.01-2.20 (br., m, —COCH$_3$). The contents of acetyl groups are 11.6%.

Embodiment 16

Acetylation of Enriched Polysaccharides, 83018-16-16 (13)

A total of 300 mg of enriched polysaccharides, 100×-032889-3500 DaPs (12) was accurately weighed into a 50 mL of round bottom flask and 24 mL of DMSO was added. The solution was settled at ambient temperature for 24 h and 1.8 mL of pyridine as well as 1.5 mL of acetic anhydride were successively added with stirring in an ice water bath for 30 min and then allowed warm to room temperature for 1.5 h. After 2 hours, water was added to quench the reaction and the solution was transferred into a dialysis membrane tube with 3500 Da. The reaction product was dialyzed until no pyridine was smelled and the dialysate was lyophilized to yield a white enriched acetylated polysaccharide product, 83018-16-16 (13). IR (KBr) vmax.: 3428, 1738, 1639, 1375, 1246, and 1042 cm$^{-1}$. $^1$H NMR (400 MHz, D$_2$O) δ (ppm): 2.00-2.19 (br. m, —COCH$_3$). The contents of acetyl groups are 20.2%.

Additional Embodiments

Pharmaceutical Formulations

In some embodiments, the active ingredients and mixtures of active ingredients can be used, for example, in pharmaceutical formulations comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents can be provided in the pharmaceutical formulation. For example, sodium benzoate, ascorbic acid and esters of p-hydroxybenzoic acid can be added as preservatives. In addition, antioxidants and suspending agents can be used.

Pharmaceutical formulations of the active ingredients can be formulated and used as tablets, capsules, or elixirs for oral administration. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical formulations can contain minor amounts of nontoxic auxiliary substances, such as wetting agents, pH buffering agents, and the like. If desired, absorption enhancing preparations (for example, liposomes), can be utilized.

For injection, the agents of the invention can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the pharmaceutical formulations disclosed herein, in particular, those formulated as solutions, can be administered parenterally, such as by intravenous injection. The active ingredients can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical formulations for parenteral administration include aqueous solutions of the active ingredients in water-soluble form. Additionally, suspensions of the active ingredients can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents that increase the solubility of the ingredients to allow for the preparation of highly concentrated solutions. In some embodiments, of the pharmaceutical formulations, the vehicle is a lipophilic solvent, fatty oil, organic oil, or liposome. In some embodiments, the vehicle is sesame oil, soybean, grapefruit or almond oils, or synthetic fatty acid esters, such as ethyl oleate or triglycerides, or liposomes.

Pharmaceutical preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active ingredient doses. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active ingredient doses. Such formulations can be made using methods known in the art. See, for example, U.S. Pat. No. 5,733,888 (injectable pharmaceutical formulations); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The pharmaceutical formulations can be manufactured in a manner that is itself known, for example, by means of conventional mixing, dissolving, granulating, dragee-making, levitating, emulsifying, encapsulating, entrapping, or lyophilizing processes. In some embodiments, the pharmaceutical formulation further comprises an excipient. In some embodiments, the pharmaceutical formulation is prepared for oral use. In some embodiments, the excipient is sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

To formulate the dosage including one or more active ingredients disclosed herein, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing ingredients, sweeteners, fragrances, colorants, preservatives and the like can be added to the administered formulation of the compound of the invention, particularly when the compound is to be administered orally.

Further disclosed herein are various pharmaceutical formulations well known in the pharmaceutical art for uses that include intraocular, intranasal, and intraauricular delivery. Pharmaceutical formulations include aqueous ophthalmic solutions of the active ingredients in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. These formulations can be used as an anti-inflammatory for the eye, for example. All of the above-mentioned references are incorporated herein by reference in their entireties. Such suitable pharmaceutical formulations are most often and preferably formulated to be sterile, isotonic and buffered for stability and comfort. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers.

The pharmaceutical formulations described herein can be administered by either oral or non-oral pathways. When administered orally, pharmaceutical formulations can be administered in capsule, tablet, granule, spray, syrup, or other such form. Pharmaceutical formulations also can be brewed, as with a tea, or formed by dissolving a powdered pharmaceutical formulation into a fluid, typically water, fruit or vegetable juice, or milk. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it can be administered topically as deemed appropriate by those of skill in the art for bringing the ingredients of the invention into optimal contact with living tissue.

Agents intended to be administered intracellularly can be administered using techniques well known to those of ordinary skill in the art. For example, such agents can be encapsulated into liposomes, then administered by any of the methods described herein. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

In some embodiments, the pharmaceutical formulations described herein are formulated into a single pill or tablet or gummy or capsule, or lozenge. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than,"

"less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of making *aloe* acetylated polysaccharides, the method comprising:
   a) providing *aloe* comprising *aloe* polysaccharides, wherein the polysaccharides comprise glucomannan, glucogalactomannan, galactomannan, mannan and their acetylated forms; followed by
   b) purifying the *aloe* polysaccharides to 1-90% purity by weight; followed by
   c) providing an acetylation agent; followed by
   d) providing a catalyst; followed by
   e) mixing the acetylation agent and catalyst with the *aloe* polysaccharides, thereby manufacturing acetylated *aloe* polysaccharides, wherein the acetylation exceeds that of the *aloe* polysaccharides in step a); and followed by
   f) purifying the acetylated *aloe* polysaccharides.

2. The method of claim 1, wherein the *aloe* polysaccharides are in a powder formulation.

3. The method of claim 1, wherein the *aloe* polysaccharides comprise mannose moieties.

4. The method of claim 3, wherein the mannose moieties comprise hydroxyl groups, wherein the hydroxyl groups are capable of being acetylated.

5. The method of claim 4, wherein the acetylated *aloe* polysaccharides comprise acetyl groups on the mannose moieties at mannose sites 2, 3 and/or 6.

6. The method of claim 1, wherein the acetylation agent is acetic anhydride $(CH_3CO)_2O$, acetyl chloride, and acetic acid.

7. The method of claim 1, wherein the catalyst is pyridine, sodium hydroxide, potassium hydroxide, sodium carbonate, or potassium carbonate and solvent.

8. The method of claim 1, wherein the purifying step of step b) is performed by ethanol precipitation.

9. The method of claim 1, wherein the purifying step of step f) is performed by dialysis.

10. The method of claim 1, wherein the acetylation agent is acetic anhydride $(CH_3CO)_2O$.

* * * * *

UNITED STATES PATENT AND TRADEMARK OFFICE
CERTIFICATE OF CORRECTION

PATENT NO. : 11,547,719 B2
APPLICATION NO. : 17/034672
DATED : January 10, 2023
INVENTOR(S) : Joosang Park et al.

It is certified that error appears in the above-identified patent and that said Letters Patent is hereby corrected as shown below:

On the Title Page

On Page 2, Column 1, Lines 2-3, under Other Publications, delete "administation" and insert --administration--.

On Page 2, Column 1, Line 6, under Other Publications, delete "(Cholorophta)," and insert --(Chlorophyta),--.

On Page 2, Column 1, Line 8, under Other Publications, delete "toleraabilty" and insert --tolerability--.

In the Specification

In Column 2, Line 47, delete "thereof," and insert --thereof.--.

In Column 2, Line 61, delete "actylated" and insert --acetylated--.

In Column 3, Line 30, delete "thereof," and insert --thereof.--.

In Column 3, Line 45, delete "actylated" and insert --acetylated--.

In Column 6, Line 64, after "(1)" insert --.--.

In Column 7, Line 5, after "(3)" insert --.--.

In Column 8, Line 15, delete "dimethylhydentoin" and insert --dimethylhydantoin--.

In Column 8, Line 19, delete ""cataylst."" and insert --"catalyst."--.

In Column 11, Line 39, delete "µL," and insert --µL--.

Signed and Sealed this
Twenty-fifth Day of April, 2023

Katherine Kelly Vidal
*Director of the United States Patent and Trademark Office*

CERTIFICATE OF CORRECTION (continued)
U.S. Pat. No. 11,547,719 B2

In Column 12, Line 32 (Approx.), delete "aceylated" and insert --acetylated--.

In Column 15, Line 66, delete "68.6 ( )" and insert --68.6 (),--.

In Column 16, Line 38 (Approx.), after "12.1%" insert --.--.

In Column 17, Line 28, after "13.5%" insert --.--.

In Column 17, Line 37, delete "millieter" and insert --milliliter--.

In Column 20, Line 46, delete "methasilicate" and insert --metasilicate--.

In Column 21, Line 35, delete "intreperitoneally," and insert --intraperitoneally,--.